United States Patent [19]
Morioka et al.

[11] Patent Number: 6,030,820
[45] Date of Patent: *Feb. 29, 2000

[54] PROCESS FOR PRODUCING HIGH-PURITY ERYTHRITOL CRYSTAL

[75] Inventors: Satoshi Morioka, Yokohama; Takahiro Abe, Tokyo; Toshihiro Maeda, Sendai; Arihiro Taki, Omiya; Katsuhiko Sawada, Tokyo; Hiroaki Ishitsuka, Mohka, all of Japan

[73] Assignees: Mitsubishi Chemical Corporation, Japan; Nikken Chemicals Co., Ltd., Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/165,796

[22] Filed: Oct. 2, 1998

[30] Foreign Application Priority Data

Oct. 7, 1997 [JP] Japan .................................. 9-290281

[51] Int. Cl.⁷ .................................. C12P 7/18; C12P 1/02; C07C 27/26; C07C 31/18
[52] U.S. Cl. .................... 435/158; 435/171; 435/911; 568/852; 568/868; 568/872
[58] Field of Search .................. 435/158, 171, 435/911; 568/868, 852, 872

[56] References Cited

U.S. PATENT DOCUMENTS

| | | |
|---|---|---|
| 3,284,419 | 11/1966 | Helferich . |
| 3,756,917 | 9/1973 | Dezeeuw et al. . |
| 4,379,751 | 4/1983 | Yoritomi et al. . |
| 4,482,761 | 11/1984 | Chao et al. . |
| 4,906,569 | 3/1990 | Maeda et al. ............................ 435/158 |
| 5,202,507 | 4/1993 | Oshima et al. ......................... 568/868 |

FOREIGN PATENT DOCUMENTS

| | | |
|---|---|---|
| 0 262 463 | 4/1983 | European Pat. Off. . |
| 0327016 | 8/1989 | European Pat. Off. . |
| 0 525 659 | 2/1993 | European Pat. Off. . |
| 47-41549 | 10/1972 | Japan . |
| 49-118889 | 11/1974 | Japan . |
| 60-110295 | 6/1985 | Japan . |
| 61-31091 | 2/1986 | Japan . |
| 63-196298 | 8/1988 | Japan . |
| 9-252765 | 9/1997 | Japan . |

OTHER PUBLICATIONS

Chemical Abstracts vol. 112 (1990) No. 13 p. 612 XP–002096380.
Chemical Abstracts, XP–002096382, vol. 80, May 27, 1974, No. 21 (p. 163).
Chemical Abstracts, XP–002096383, vol. 66, Apr. 24, 1967, No. 17 (p. 6795).
Chemical Abstracts, XP–002096384, vol. 125, Nov. 11, 1996, No. 20 (p. 216).
Chemical Abstracts, XP–002096385, vol. 102, Jun. 10, 1985, No. 23 (p. 634).
Chemical Abstracts, XP–002096386, vol. 76, Mar. 20, 1972, No. 12 (p. 94).
JP 05 137585 Jun. 1, 1993 (Abstract) Derwent Publications Ltd. (Mitsubishi).

*Primary Examiner*—Herbert J. Lilling
*Attorney, Agent, or Firm*—Nixon & Vanderhye

[57] ABSTRACT

A process for producing a high-purity erythritol crystal comprising a crystallization step of subjecting an erythritol-containing aqueous solution as a raw solution to crystallization, wherein an erythritol concentration of said erythritol-containing aqueous solution is adjusted to 30 to 60% by weight at the beginning of the crystallization step; said erythritol-containing aqueous solution is cooled at a cooling rate of not more than 20° C./hour; a seed crystal of erythritol is added to said erythritol-containing aqueous solution in the course of the cooling, and the solution is cooled to not more than 20° C. Such a process for producing a high-purity erythritol crystal of the present invention has a still higher purity and is further improved in crystal shape as compared to those produced by conventional processes.

7 Claims, 5 Drawing Sheets

PROCESS FOR PRODUCING HIGH-PURITY ERYTHRITOL CRYSTAL

BACKGROUND OF THE INVENTION

The present invention relates to a process for producing a high-purity erythritol crystal.

Erythritol (i.e., meso-erythritol) is useful not only as a sweetening agent but also as an intermediate product of medicines, industrial chemicals or the like. The erythritol can be industrially produced by culturing erythritol-producing microorganisms in an aqueous culture medium under aerobic conditions, for example, using glucose as a raw material.

The erythritol-containing culture solution contains various liquid or solid impurities. More specifically, the culture solution contains, as liquid impurities, by-products such as glycerol. Further, in the case where purified glucose obtained by enzyme-saccharization of starch, etc., is used as a raw material, the culture solution also contains, as liquid impurities, oligosaccharides such as di- or more saccharides inherently contained in the raw purified glucose, reaction products of these oligosaccharides, polysaccharides having a β-1,4 bond which are composed mainly of glucose, or the like. In addition, the culture solution contains, as solid impurities, suspended fine substances in addition to microbe.

High-purity erythritol crystal can be produced by subjecting the above-mentioned culture solution to a process successively comprising a microbe-separating step, a chromatographic separation step and a crystallization step. As an example of these processes, there is known a method of separating and recovering erythritol from an erythritol-containing culture solution as described in Japanese Patent Publication (KOKOKU) No. 7-34748(1995).

Meanwhile, as described above, since erythritol is mainly used as a sweetening agent, it is preferred that the purity of erythritol produced be as high as possible. Further, from the standpoints of separating crystal from a slurry and preventing the agglomeration of fine powder produced due to inevitable fracture of crystal products, it is preferred that the crystal produced be in the form of a single-crystal having an appropriate size.

In addition, in the microbe-separating step of the above-mentioned process, when the removal of microbe and the suspended fine substances is insufficient, safe operations of the subsequent steps cannot be assured. For example, the unsatisfactory removal results in not only clogging of a resin column in the chromatographic separation step and failure of a heat exchanger by burning and sticking to the surface of its tubes or plates, but also lowering a purity of erythritol produced. Therefore, the microbe-separating step is extremely important in an industrial-scale process for the production of high-purity erythritol crystal. However, hitherto, the microbe-separating step in the process for producing erythritol has not been studied to a sufficient extent. For example, in Examples of Japanese Patent Publication (KOKOKU) No. 7-34748(1995), it has been only described to use a centrifugal separator in the microbe-separating step.

Further, in the industrial-scale production of high-purity erythritol crystal, it is also important that the production process thereof can be safely and stably conducted. As one step of the process to be stably conducted, there is exemplified a crystal separation step of separating an erythritol crystal from an erythritol crystal-containing slurry recovered from the crystallization step. That is, in the crystal separation step, there has been generally used a centrifugal separator. In this case, when erythritol crystal obtained by solid-liquid separation is unevenly distributed in the centrifugal separator, the stable operation of the centrifugal separator cannot be assured.

Furthermore, in the industrial production of high-purity erythritol crystal, it has also been demanded to produce such an erythritol crystal not only having a high purity but also free from inclusion of fin powder to avoid the agglomeration of crystal products.

The present invention has been attained in view of the above-mentioned circumstances, and is constituted by a group of inventions which are associated each other.

SUMMARY OF THE INVENTION

It is an object of the present invention to provide a process for producing a high-purity erythritol crystal which has a still higher purity and is further improved in crystal shape as compared to those produced by conventional processes.

To accomplish the aim, in a first aspect of the present invention, there is provided a process for producing a high-purity erythritol crystal comprising a crystallization step of subjecting an erythritol-containing aqueous solution as a raw solution to crystallization and a crystal separation step of separating an erythritol crystal from an erythritol crystal-containing slurry obtained in the crystallization step, wherein an erythritol concentration of the erythritol-containing aqueous solution is adjusted to 30 to 60% by weight at the beginning of the crystallization step, the erythritol-containing aqueous solution is cooled at a cooling rate of not more than 20° C./hour, a seed crystal of erythritol is added to the erythritol-containing aqueous solution in the course of the cooling; and after cooling to not more than 20° C., the produced erythritol crystal is separated from said slurry.

It is another object of the present invention to provide a process for producing a high-purity erythritol crystal, which comprises successively a microbe-separating step, a chromatographic separation step and crystallization step, and is capable of removing solid impurities in the microbe-separating step with a high efficiency.

To accomplish the aim, in a second aspect of the present invention, there is provided a process for producing a high-purity erythritol crystal, which comprises a microbe-separating step of separating microbe from an erythritol-containing culture solution as a raw solution, a chromatographic separation step of subjecting a purified solution recovered from the microbe-separating step to chromatographic separation, and a crystallization step of subjecting an erythritol fraction recovered from the chromatographic separation step to crystallization to obtain an erythritol, wherein the microbe-separating step is conducted by a cross-flow filtration method using a ceramic membrane or an organic membrane, maintaining the temperature of the solution treated in the microbe-separating step at a temperature of 50 to 90° C.

It is an other object of the present invention to provide a process for producing a high-purity erythritol crystal, which is improved so as to stably conduct the crystal separation step following the crystallization step.

To accomplish the aim, in a third aspect of the present invention, there is provided a process for producing a high-purity erythritol crystal, which comprises a crystallization step of subjecting an erythritol-containing aqueous solution to crystallization, and a crystal separation step of separating an erythritol crystal from an erythritol crystal-containing slurry obtained in the crystallization step, wherein a centrifugal separator of a type in which the slurry is dispersed in the circumferential direction of a filtering surface and impinged against the filtering surface, is used in the crystal separation step.

It is a still other object of the present invention to provide a process for producing a high-purity erythritol crystal, which is improved so as to obtain an erythritol crystal having a uniform particle size.

To accomplish the aim, in a fourth aspect of the present invention, there is provided a process for producing a high-purity erythritol crystal, which comprises a crystallization step of subjecting an erythritol-containing aqueous solution to crystallization, and a crystal separation step of separating an erythritol crystal from an erythritol crystal-containing slurry obtained in the crystallization step, wherein the crystal separation step is conducted by centrifugal separation using a centrifugal force of 50 to 500 G, and a wet erythritol crystal separated by the centrifugal separation is spray-washed with water at a temperature of not more than 20° C., the amount of water used for the spray-washing being 0.1 to 1 part by weight based on one part by weight of said wet erythritol crystal.

DETAILED DESCRIPTION OF THE INVENTION

Figure 1:
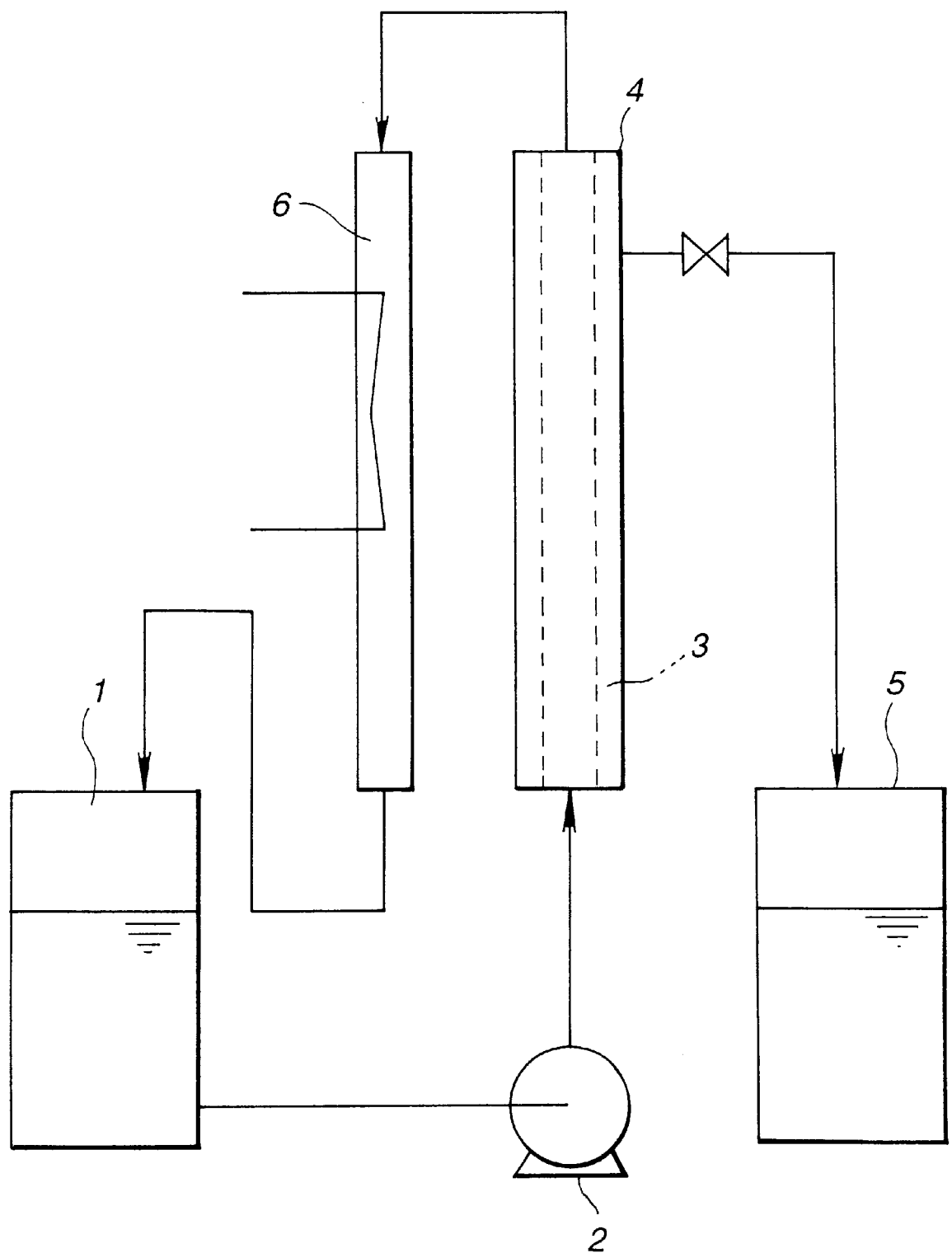
FIG. 1 is a schematic conceptional view showing a preferred microbe-separating step in a process according to the present invention.

The present invention is described in detail below.

The erythritol-containing aqueous solution used in the present invention, is not particularly restricted, but typical examples of these solutions may include (1) an erythritol fraction recovered from a chromatographic separation step in the process comprising a microbe-separating step of removing microbe from an erythritol-containing culture solution as a raw solution, the chromatographic separation step of subjecting a purified solution recovered from the microbe-separating step to chromatographic separation, and a crystallization step of subjecting the erythritol fraction recovered from the chromatographic separation step to crystallization for producing an erythritol crystal, or (2) a crystal separation mother liquor recovered from the crystallization step of the above-mentioned process.

First, the above-mentioned process is briefly explained. The erythritol-containing culture solution may be produced by culturing erythritol-producing microorganisms in an aqueous culture medium under aerobic conditions. The culturing method is not particularly restricted, and any known methods can be used therefor.

For example, as raw culture materials, there may be used crystal sucrose, crystal glucose or purified glucose obtained by subjecting starch to enzyme saccharification method or the like. Incidentally, the purified glucose may usually have a glucose content of 93 to 97% by weight, and the remainder of the purified glucose may be composed of oligosaccharides such as di-, tri- or more saccharides.

Whereas, as the erythritol-producing microorganisms, there may be used genus *Aureobasidium* (Japanese Patent Application Laid-open (KOKAI) No. 61-31091(1986)), *Moniliella tomentosa var. pollinis* (Japanese Patent Applications Laid-open (KOKAI) Nos. 60-110295 to 110298 (1985)), *Trichosporonoides megachiliensis* (Japanese Patent Application Laid-open (KOKAI) No. 63-196298(1988), former name: genus *Aureobasidium*), *Trichos-oronoides oedocephalis* (Japanese Patent Application Laid-open (KOKAI) No. 9-252765(1997)), *Candida zeylanoides* (ATCC15585), *Torulopsis fomata* (ATCC15586), etc., (Japanese Patent Application Laid-open (KOKAI) No. 49-118889(1974)), *Candida lipolytica* (U.S. Pat. No. 3,756, 917), genus Trigonopsis, genus Candida (Japanese Patent Publication (KOKOKU) No. 47-41549(1972)), or the like.

In addition, as inorganic salts used in the culture medium, there may be exemplified $KH_2PO_4$, $MgSO_4$, $CaCl_2$, $K_2SO_4$, $CaSO_4$, $FeSO_4$, $MnSO_4$, $ZnSO_4$, $(NH_4)_2HPO_4$ or the like. As nitrogen sources, there may be exemplified $(NH_4)_2SO_4$, $CO(NH_2)_2$, $NH_4Cl$, $NH_4NO_3$ or the like. As nutrient sources, there may be exemplified corn-steeped liquor, soybean meal, various amino acids, peptone, thiamine, yeast extract or the like.

The above-mentioned process itself which successively comprises the microbe-separating step, the chromatographic separation step and the crystallization step, is basically already known, for example, as described in Japanese Patent Publication (KOKOKU) No. 7-34748(1995). The outline of the process is as follows.

That is, the purified solution obtained from the microbe-separating step, is subjected to a concentration step, preferably after a softening step, and then fed to the chromatographic separation step. The erythritol fraction recovered from the chromatographic separation step is also subjected to a concentration step, preferably after an activated-carbon treatment and/or desalting treatment, and then fed to the crystallization step and the crystal separation step. Thereafter, the erythritol crystal separated at the crystal separation step is successively subjected to drying and sieving steps to obtain a high-purity crystal product.

In the present invention, according to the finding of the present inventors, it is preferred that the microbe-separating step be conducted by a cross-flow filtration method using a ceramic membrane or an organic membrane while maintaining the solution to be treated at a temperature of 50 to 90° C. The reasons therefor are as follows.

(1) In the case where the microbe-separating step is conducted by the cross-flow filtration method, solid impurities can be effectively and highly removed from the erythritol-containing culture solution containing various liquid or solid impurities. In addition, when the purified solution recovered from the microbe-separating step is concentrated in order to increase an efficiency of the chromatographic separation, occurrence of foaming phenomenon can be remarkably prevented. Accordingly, by conducting the microbe-separating step by the cross-flow filtration method using a ceramic membrane or an organic membrane, it becomes possible to produce a high-purity erythritol crystal in industrially advantageous.

(2) Even though the cross-flow filtration method is used, it is still difficult to completely remove the impurities, so that the purified solution obtained from the microbe-separating step still contains various impurities serving as nutrient sources for various germs. For this reason, in the case where the culture solution to be treated in the microbe-separating step has a low temperature, the breeding of various germs is caused. This results in not only the production of low-quality erythritol crystal which is unfavorable when used as sweeteners or medicines, but also, for example, clogging of a resin column in the chromatographic separation step or failure of a heat exchanger by burning and sticking to the surface of its tubes or plates. Therefore, in accordance with the present invention, the culture solution to be treated is maintained at not less than 50° C. during the microbe-separating step in order to prevent the breeding of various germs. Incidentally, when the temperature of the culture solution to be treated is more than 90° C., there arises such a disadvantage that the culture solution to be treated undergoes abrupt increase in degree of coloring thereof.

The structure of the ceramic membrane (porous membrane) is not particularly restricted. The ceramic membrane may have either a single-layer structure or a two-layer structure having a fine particle layer and a supporting layer. In the two-layer structure case, the fine particle layer may have an average pore diameter of usually 0.1 to 1 μm, preferably 0.1 to 0.5 μm. As materials of the ceramic membrane, there may be exemplified silica, alumina, silica-alumina, mullite, zirconia, carbon, cordierite, silicon carbide or the like. The structure of the organic membrane is not particularly restricted. However, the organic membrane is required to be made of a material capable of showing a sufficient heat resistance at a temperature of 50 to 90° C. as described hereinafter. As such materials of the organic membrane, there may be exemplified polyolefins, polyether sulfones or the like.

In the cross-flow filtration method, there may be used such a facility comprising a circulation tank, a pump, a separation element equipped therein with a filter membrane and a filtrate reservoir. These members cooperate to constitute a circulating path for the culture solution to be treated. Preferably, a heat exchanger is disposed in the mid of the circulating path.

The cross-flow filtration method is principally a filtration method in which a liquid to be filtered is caused to flow on a surface of a membrane filter in the direction parallel therewith, thereby filtering the liquid while minimizing deposition of a filter cake layer on the membrane filter by shear force of the parallel flow. Accordingly, the liquid to be filtered (raw solution) is fed from one end of the circulating path surrounded by the membrane filter and filtered while flowing therethrough. A filtrate is discharged through the membrane filter in the direction perpendicular to the circulating path, whereas a microbe-concentrated liquid is discharged from the other end of the circulating path.

The cross-flow filtration may be conducted in a batch operation. In the present invention, the cross-flow filtration method comprises a series of operations including (A) microbe-concentration and filtration, (B) water-added filtration, (C) additional microbe-concentration and filtration, (D) washing with water and (E) regeneration. Especially, in the preferred embodiment of the present invention, the additional concentration and filtration (C) can be conducted.

The microbe-concentration and filtration (A) may be conducted as follows. In the microbe-separating step (cross-flow filtration apparatus) as shown in FIG. 1, after a predetermined amount of an erythritol-containing culture solution is fed into a circulation tank 1, a pump 2 is operated to initiate circulation of the culture solution by passing through a filter membrane 3 and a heat exchanger 6 and returning to the circulation tank 1. The purified solution (filtrate) passed through the filter membrane 3, is received in a filtrate reservoir 5. When the concentration of microbe in the circulated culture solution reaches a predetermined value, the microbe-concentration and filtration is terminated. Incidentally, the erythritol-containing culture solution may be heated to the above-mentioned temperature range, if necessary, before feeding to the circulation tank 1, or the circulated culture solution may be maintained within the temperature range by using the heat exchanger 6 (these heating or temperature conditions can also be commonly applied to the water-added filtration (B) and the additional concentration and filtration (C) described hereinafter).

In the water-added filtration (B), the same circulating operation as described above may be conducted by continuously adding water to the concentrated solution in the circulation tank 1 while maintaining a constant level of the concentrated solution. The purified solution (filtrate) passed through the filter membrane 3 is received in the filtrate reservoir 5. Incidentally, water to be added may be heated to the above-mentioned temperature range, if required, before feeding to the circulation tank 1.

The additional concentration and filtration (C) may be conducted to accomplish so-called squeeze-out. In this operation, after the addition of water to the circulation tank 1 (in the water-added filtration (B)) is stopped, the same circulating operation as described above is repeated. The purified solution (filtrate) passed through the filter membrane 3, is received in the filtrate reservoir 5.

The washing with water (D) and the regeneration (E) may be conducted by ordinary methods. As regenerants, there may be used, for example, an aqueous solution containing about 0.5% by weight of NaOH and about 0.2% by weight of NaClO. The operations (D) and (E) may be conducted at a temperature of usually about 50 to about 70° C.

The above-mentioned microbe-concentration and filtration (A), water-added filtration (B) and additional concentration and filtration (C) may be usually conducted under such conditions that the circulating flow rate is 1 to 10 m/s and the pressure difference through membrane is 0.1 to 10 $Kg/cm^2$. In the microbe-concentration and filtration (A) and the water-added filtration (B), the flow rate of the solution penetrating through the filter membrane may be usually 100 to 200 $liter/m^2 \cdot hour$. In the additional concentration and filtration (C), the flow rate of the solution penetrating through the filter membrane is gradually decreased. In the present invention, it is preferred that when the penetrating flow rate reaches about 50 $liter/m^2 \cdot hour$, the additional concentration and filtration is stopped, and the washing with water (D) and the regeneration (E) are initiated. That is, according to the finding of the present inventors, in the case where the erythritol-containing culture solution is excessively subjected to the additional concentration and filtration beyond the above-specified range, the clogging of the filter membrane 3 tends to be abruptly accelerated, thereby adversely affecting an operation of the succeeding microbe-separating step.

In the present invention, the pH of the erythritol-containing culture solution to be treated at the above microbe-separating step, is preferably adjusted to 3.5 to 5.5. Specifically, when the pH of the erythritol-containing culture solution obtained from the preceding culturing step is controlled to the range close to an isoelectric point thereof, proteins dissolved in the culture solution are precipitated into flocks, thereby further facilitating removal of the proteins. The pH of the culture solution may be adjusted by using, for example, an aqueous solution containing an appropriate alkali such as sodium hydroxide or the like.

The softening step is carried out in order to maintain a good separating efficiency in the following chromatographic separation step. As ion-exchange resins, there may be exemplified sulfonic acid-type strongly acidic cation exchange resins or carboxylic acid-type weakly acidic cation exchange resins both of which are used in the form of a Na type. The purified solution is passed through a resin-filled tower or column to replace Ca ions or Mg ions therein with Na ions, thereby removing the Ca or Mg ions therefrom. The cation exchange resins which have been converted from Na type into Ca and/or Mg types, may be regenerated to convert again these resins into Na type, and used repeatedly. In the case of the sulfonic acid-type resins, the resins may be regenerated by using an aqueous NaCl solution. In the case of the carboxylic acid-type resins, the resins may be first converted into H type resins by using strong acids such as HCl or $H_2SO_4$, and then regenerated to Na type resins by using an aqueous NaOH solution. Among these methods, the method using carboxylic acid-type weakly acidic cation exchange resins (Na type) is preferred.

In the present invention, according to the finding of the present inventors, it is preferred that the above softening step be conducted while maintaining the temperature of the purified solution at 50 to 90° C. The reasons therefor are as follows.

The purified solution obtained from the microbe-separating step, still contains various impurities serving as nutrient sources for various germs, resulting in breeding of various germs. Accordingly, if the breeding of various germs is inhibited to a sufficient extent at an initial stage of the process, not only inclusion of the impurities in erythritol crystal but also occurrence of the other disadvantages, e.g., clogging of the resin column in the chromatographic separation step or failure of the heat exchanger by burning and sticking to the surface of its tubes or plates, can be effectively prevented, so that it becomes possible to produce a high-purity erythritol crystal in industrially advantageous.

The purified solution to be treated in the softening step, can be maintained at a temperature of 50 to 90° C. by a heating means disposed in the above-mentioned resin-filled tower or column, or the pre-heating of the purified solution before feeding to the softening step. When the temperature of the purified solution is less than 50° C., the inclusion of various germs in the purified solution and the breeding of various germs cannot be sufficiently prevented. On the other hand, when the temperature of the purified solution is more than 90° C., there arise disadvantages such as coloring of the culture solution treated or deterioration of resin used.

The concentration step conducted before the chromatographic separation step, aims to increase an efficiency of the chromatographic separation. The purified culture solution is concentrated until the solid content dissolved therein reaches usually 30 to 70% by weight, preferably 35 to 45% by weight.

Incidentally, in general, as concentrators used for concentrating an aqueous solution containing organic substances, there are known, for example, a jacketed-type evaporator which is heated by flowing steam along an outer wall of the container, a forced circulation-type evaporator equipped with a circulating pump for increasing a flow rate of fluid passed through a heating pipe, a rising or falling film-type evaporator belonging to a long tube vertical evaporator, or the like.

The concentrator used in the concentration step, is not particularly restricted as long as any of the above-mentioned heating systems is used. According to the finding of the present inventors, the forced circulation-type evaporators or film-type evaporators are preferred, and the film-type evaporators are more preferred. In general, among them, the falling film-type evaporators are still more preferred. The reasons therefor are as follows.

Since the purified solution obtained from the microbe-separating step contains various impurities as described above, the solution tend to contain colored components, especially those produced by a Mailard reaction between glucose and amino acid. The production of such colored components is promoted with heating time. Also, since the culture solution contains soluble proteins, there is caused a foaming phenomenon upon concentration, so that it is not necessarily easy to conduct stable concentration of the purified solution. In such a case, it is generally difficult to satisfy heat transfer conditions for inhibiting occurrence of the foaming phenomenon, especially upon concentration, by using the jacketed evaporator. On the other hand, the forced circulation-type evaporators or the film-type evaporators can prevent occurrence of the foaming phenomenon upon concentration over a wide range of heat transfer conditions.

The above-mentioned falling film-type evaporator is divided into an evaporator section and a falling film-forming section in view of a functional structure thereof. The falling film-forming section may be of either (1) a plate-type or (2) a shell and tube-type. In the concentration step, the operation pressure is preferably 70 to 300 torr, and the fluid temperature is preferably 45 to 80° C. When the operation pressure is less than 70 torr, violent foaming tends to be generated, thereby causing loss due to entrainment and further disabling stable operation of the evaporator. In addition, the low operation pressure tends to decrease the fluid temperature, so that contamination by various germs might be caused. On the other hand, when the operation pressure is more than 300 torr, the fluid temperature is increased, so that there is a tendency that coloring of the solution is disadvantageously promoted.

The chromatographic separation step comprises passing the purified solution through a separation tower filled with alkali metal type or ammonium type of strongly acidic cation exchange resins, eluting components absorbed in the resins with water to discharge an effluent containing the eluted components, and separating a fraction composed mainly of erythritol from the effluent. The obtained fraction composed mainly of erythritol may usually contain erythritol in an amount of 3 to 30% by weight.

In the above-mentioned chromatographic separation step (at the separation tower), the respective components absorbed in the cation exchange resins as a separating agent may be eluted out in the following manner. That is, after salts, colored components and high-molecular weight polysaccharides (hereinafter referred to merely as "first impurities") are first eluted, oligosaccharides such as di- or more saccharides and by-products other than glycerol (hereinafter referred to merely as "second impurities") are eluted and then erythritol and glycerol are finally eluted (see Japanese Patent Publication (KOKOKU) No. 7-34748 (1995)). Accordingly, in the chromatographic separation step, after the first and second impurities (hereinafter referred to merely as "impurities") are eluted, the erythritol fraction (composed of erythritol and glycerol) is then eluted and recovered. Next, the fraction recovered is subjected to crystallization treatment, thereby obtaining a high-purity erythritol crystal.

Meanwhile, in general, it is difficult to completely separate the erythritol fraction and the impurity fraction from each other. Therefore, after the erythritol fraction eluted together with the impurity fraction (hereinafter referred to merely as "overlapped fraction") is removed, the erythritol fraction free from impurities is recovered.

However, the amount of the overlapped fraction is increased as the purity of the erythritol fraction recovered becomes higher, so that the recovery percentage of the aimed high-purity erythritol crystal is lowered.

In accordance with the present invention, the following improved chromatographic separation step is preferably adopted in order to obtain a high purity erythritol crystal at a high recovery percentage and reduce a load applied to the concentration step after the chromatographic separation step.

That is, in the process according to the present invention, the following operations of the chromatographic separation are preferably conducted using a separation tower filled with alkali metal type or ammonium type of strongly acidic cation exchange resins:

(1) Feeding a predetermined amount of the purified solution to the top of the separation tower.

(2) Circulating water removed from a bottom of the separation tower to the top thereof, thereby developing the respective components absorbed by the resins and moving the impurity fractions toward the bottom side of the separation tower.

(3) Feeding water to the top of the separation tower, thereby removing the impurity fraction from the bottom of the separation tower.

(4) Removing the overlapped fraction composed of the erythritol fraction and the impurity fractions from the bottom of the separation tower and circulating the overlapped fraction to the top of the separation tower, thereby moving the erythritol fraction toward the bottom side of the separation tower.

(5) Feeding water into the separation tower at an appropriate portion where no overlapped fraction exists, thereby removing and recovering the erythritol fraction from the bottom of the separation tower.

Figure 3:
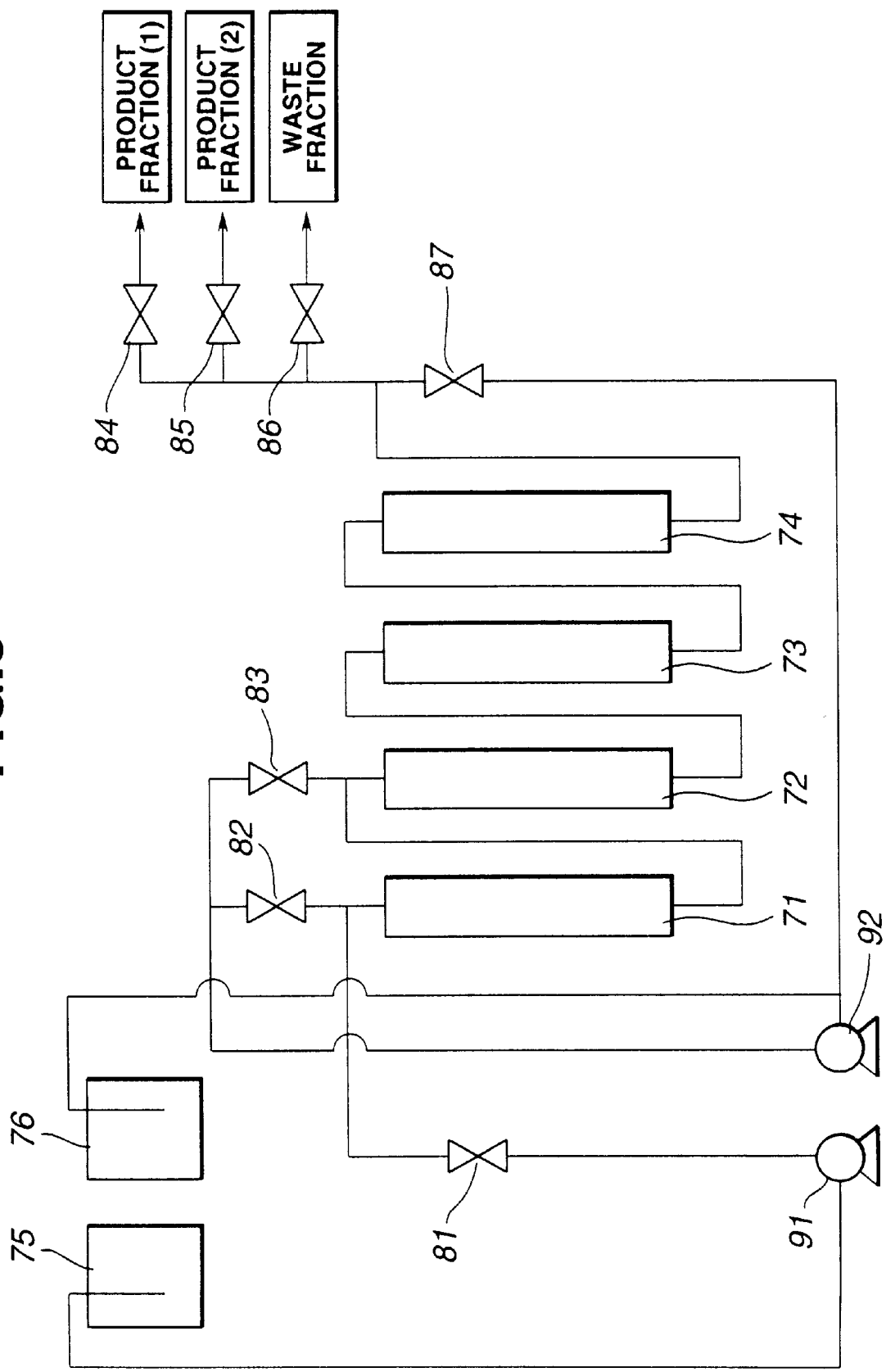
FIG. 3 is a schematic conceptional view showing a facility usable in the preferred chromatographic separation step in a process according to the present invention.

In the above-mentioned chromatographic separation step, there may be used the separation tower filled with alkali metal type or ammonium type strongly acidic cation exchange resins. Such a separation tower is made by filling a water slurry of the resins in a column. The amount of resins filled (length of the separation tower) may be appropriately determined such that the separation tower has a good separation capacity required for treating the solution. The separation tower may preferably have a divided structure composed of multiple sections as shown in FIG. 3 and described in detail hereinafter, from the standpoint of an operability thereof, though those having an integrated structure are also usable.

Figure 2:
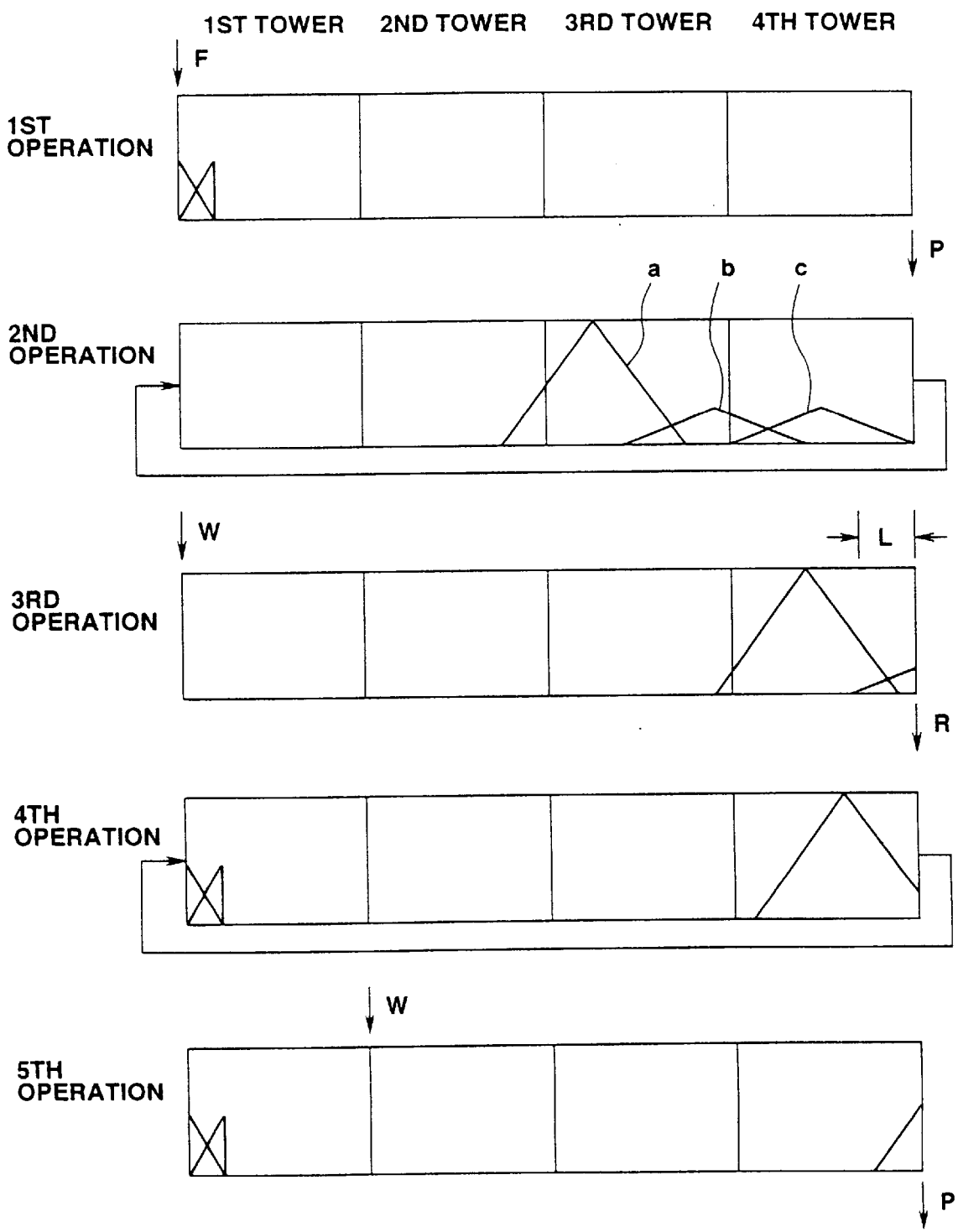
FIG. 2 is a schematic conceptional view showing movement of respective components in a preferred chromatographic separation step in a process according to the present invention.

The chromatographic separation may be conducted according to the following operations as illustrated in FIG. 2. Incidentally, FIG. 2 shows operations following a final operation (fifth operation) of the previous chromatographic separation step. In addition, the respective operations as shown in FIG. 2 are represented with respect to the condition immediately after completing each operation.

(1) A predetermined amount of the purified solution (F) is fed to a top of a separation tower (the first operation of FIG. 2), thereby removing residual erythritol (P) remaining in a fourth tower after the final operation (fifth operation of FIG. 2) of the previous chromatographic separation step.

(2) Water is removed from the bottom of the separation tower and circulated to the top thereof, thereby developing the respective components absorbed in the resins and moving the impurity fraction toward the bottom side of the separation tower (the second operation of FIG. 2). Upon conducting this operation, the separation tower is held in the condition of a closed system, and water as an eluent is circulated through the separation tower by the operation of a pump. Specifically, water on the bottom side of the separation tower is successively circulated to the top thereof, thereby developing the respective components absorbed in the resins and moving the impurity fraction toward the bottom side of the separation tower.

The second operation of FIG. 2 shows such a condition that the erythritol fraction (a) is transferred from the second tower to the third tower, the first impurity fraction (c) is transferred to the fourth tower, and the second impurity-containing fraction (b) is moved to a position between the erythritol fraction (a) and the first impurity fraction (c). Incidentally, after reaching the above condition, water removed from the bottom of the separation tower contains impurities and is, therefore, no longer usable as an eluent.

(3) Water (W) is fed to the top of the separation tower, thereby removing the impurity fraction (R) from the bottom of the separation tower (the third operation of FIG. 2). The impurity fraction removed is appropriately treated. The third operation of FIG. 2 shows such a condition that the impurity fraction is removed from the bottom of the separation tower. The term "impurity fraction" in the present invention, means such a fraction containing impurities but substantially free from the erythritol fraction, and, therefore, does not include the overlapped fraction (L) (see FIG. 2) composed of both the erythritol fraction and the impurity fraction. The overlapped fraction (L) is treated at the following fourth operation.

(4) The overlapped fraction ("L" fraction in FIG. 2) composed of the erythritol fraction and the impurity fraction is removed from the bottom of the separation tower and circulated to the top thereof, thereby moving the erythritol fraction toward the bottom side of the separation tower. Upon conducting this operation, the separation tower is held in the condition of a closed system, and the overlapped fraction (L) is removed from the bottom of the separation tower and circulated to the top thereof by the operation of a pump.

(5) Water (W) is fed into the separation tower at an appropriate position where no overlapped fraction exists, thereby removing and recovering the erythritol fraction from the bottom of the separation tower. The fifth operation of FIG. 2 shows such a condition that water is fed to a top of the second tower and a majority of the erythritol fraction (a) is removed from the bottom of the separation tower. The residual erythritol remaining in the fourth tower can be recovered by conducting the first operation of the next chromatographic separation step where the purified solution (F) is fed again to the top of the separation tower. Further, erythritol contained in the fraction transferred (circulated) to the top of the separation tower in the above fourth operation, is separated and recovered from the impurity fraction together with erythritol in the purified solution (F).

The first feature of the above-mentioned chromatographic separation resides in that after the impurity fraction which is substantially free from the erythritol fraction (a) is removed from the bottom of the separation tower, the overlapped fraction composed of the impurity fraction and the erythritol fraction (a) (which is usually successively removed and appropriately treated in order to enhance the purity of erythritol) is transferred (circulated) to the top of the separation tower, thereby increasing the recovery percentage of erythritol without decreasing the purity thereof.

Also, the second feature of the above-mentioned chromatographic separation resides in that the amount of water fed into the separation tower from outside of the system is limited to as low a level as possible, thereby reducing a load applied to the succeeding concentration step described in detail below. Therefore, in the chromatographic separation step, (1) water in the separation tower is used as an eluent (the second operation); (2) as described above, the overlapped fraction composed of the impurity fraction and the erythritol fraction, is transferred (circulated) to the top of the separation tower, thereby transferring the erythritol fraction toward the bottom side of the separation tower (the fourth operation); and (3) the amount of water fed into the separation tower in the fifth operation is reduced, thereby causing a part of the erythritol fraction to remain in the separation tower, and the residual erythritol fraction is removed and recovered from the separation tower when the purified solution is newly fed thereinto in the next chromatographic separation step (the first operation).

The activated carbon treatment step and/or desalting step may be conducted in order to remove colored components, odor components, salts or the like from the culture solution. The order of these steps may be optionally selected. The activated carbon used may be of any shape, i.e., in the form of either powder or particles. In the desalting step, there may be used a cation exchange resin column, an anion exchange resin column and a mixed bed tower containing both cation and anion exchange resins.

The concentration step immediately before the crystallization step may be conducted in order to enhance an efficiency of the succeeding crystallization step. The concentration step may be continued until the solid content dissolved in the solution reaches usually 30 to 70% by weight, preferably 40 to 60% by weight. In such a concentration step, the same evaporator and operational conditions as those for the concentration step before the chromatographic separation step, are preferably used by the same reasons as described above.

In the present invention, as erythritol-containing aqueous solutions (raw solutions to be crystallized), there may be used (1) the erythritol fraction recovered from the chromatographic separation step of the above-mentioned process, (2) the crystallization mother liquor recovered from the crystal separation step of the above-mentioned process, or the like.

In the crystallization step of the process according to the present invention, the concentration of erythritol in the raw solution to be treated is adjusted to 30 to 60% by weight at the beginning of crystallization; the solution is cooled at a cooling rate of not more than 20° C./hour; a seed crystal of erythritol is added to the raw solution in the course of cooling for the crystallization; and after cooling the solution to a temperature of not more than 20° C., and then the erythritol crystal is separated from the resultant erythritol crystal-containing slurry.

In the crystallization step of the process according to the present invention, it is preferred that after the temperature of the solution reaches 70 to 60° C. in the course of the cooling, the cooling rate of the solution is reduced, specifically to not more than 10° C./hour, and the solution is further cooled to a temperature of not more than 20° C., preferably not more than 15° C. Further, in accordance with the present invention, it is preferred that at a stage where the temperature of an erythritol-containing aqueous solution in the crystallization tank is lower than such a temperature at which the solubility of erythritol is saturated and the difference between these temperatures is not more than 15° C., a seed crystal of erythritol is added to the erythritol-containing aqueous solution in the crystallization tank. More preferably, the seed crystal of erythritol is added at the time when the temperature of the erythritol-containing aqueous solution in the crystallization tank is lower by 1 to 5° C. than the temperature at which the solubility of erythritol is saturated. The amount of the seed crystal added is not particularly restricted, but is preferably not more than 0.1% by weight, more preferably 0.001 to 0.05% by weight based on the weight of erythritol crystallized in the crystallization tank.

The apparatus used in the crystal separation step is not particularly restricted. However, according to the finding of the present inventors, it is preferred to use a centrifugal separator having such a structure that the slurry to be treated is dispersed in a circumferential direction of a filtering surface and then impinged against the filtering surface. The reasons therefor are as follows.

In the case where the most typical basket-type centrifugal separator is used, the erythritol crystal-containing slurry supplied from a single-pipe nozzle is divided into solid and liquid phases before the slurry is distributed over the whole filtering surface, resulting in uneven distribution of the erythritol crystal in the centrifugal separator and failed operation of the apparatus. These problems can be avoided by using the centrifugal separator having the above-mentioned structure.

Figure 4:
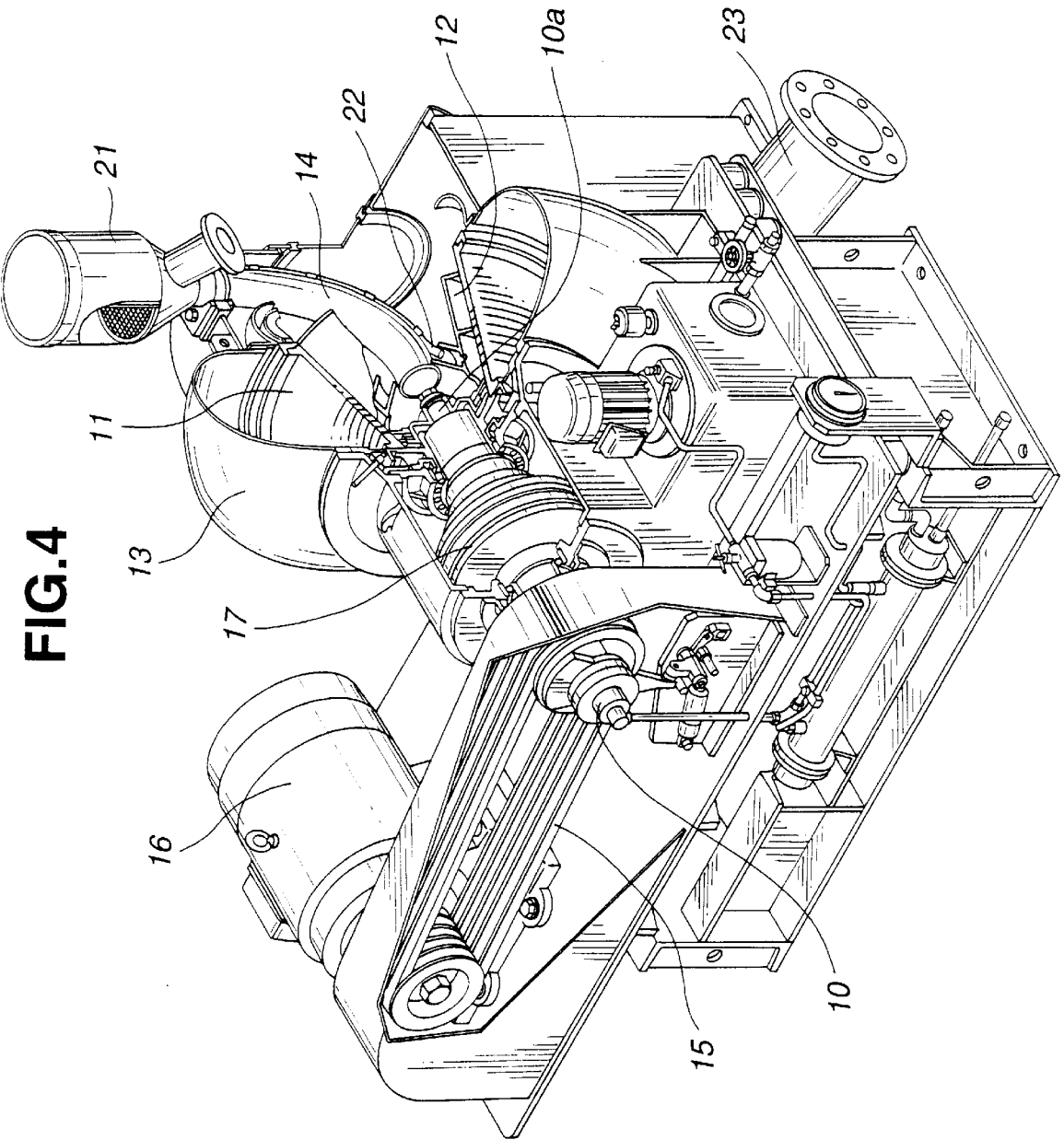
FIG. 4 is an explanatory view showing an example of a centrifugal separator preferably used in the crystal separation step in a process according to the present invention.

The centrifugal separator shown in FIG. 4 is essentially constructed by a rotatable filter member of a cylindrical shape which is gradually widened in diameter along an axial direction thereof, a screw having a contour approximately conformed to an inner periphery of the filter member and coaxially disposed within the filter member, and a slurry feed pipe mounted to a small diameter side of the filter member.

More specifically, the centrifugal separator shown in FIG. 4 comprises as main components, a basket 11 and a screw 12 both supported on a drive shaft 10, a casing 13 disposed surrounding an outer periphery of the basket 11, and a slurry feed pipe 14 inserted into the screw 12. The drive shaft 10 has a concentric double shaft structure. An outer shaft of the drive shaft 10 is driven by a motor 16 through a V-belt 15, and an inner shaft of the drive shaft 10 is driven through a synchronous speed reducer 17 at a rotating speed lower than that of the outer shaft. As a result, the basket 11 mounted on the outer shaft is rotated at a higher speed than the screw 12 mounted on the inner shaft.

Figure 5:
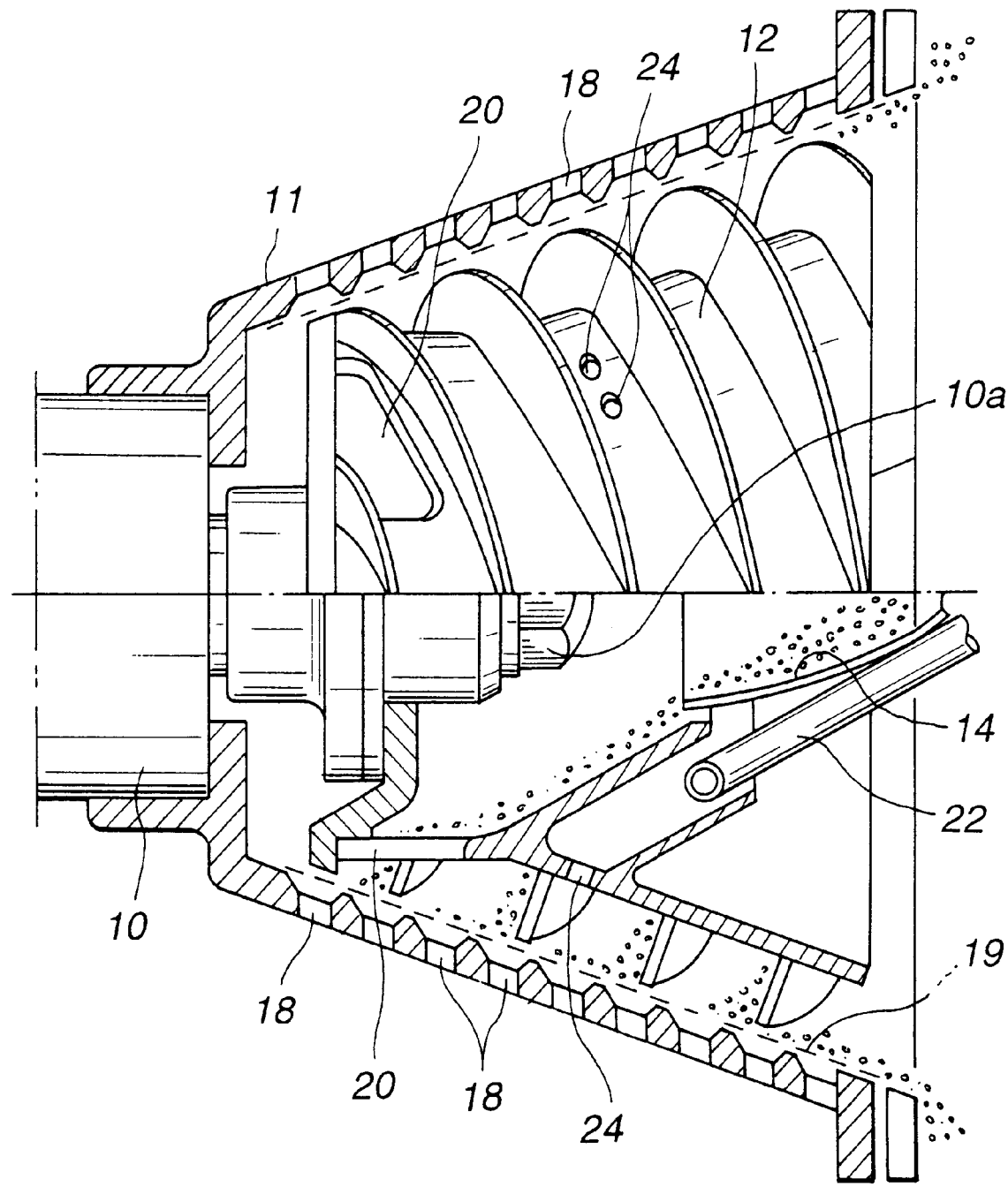
FIG. 5 is an enlarged sectional view showing essential parts of the centrifugal separator shown in FIG. 4.

As shown in FIG. 5, the basket 11 has a tapered cylindrical shape widened in diameter toward a tip end thereof, and is provided at a peripheral wall thereof with a large number of holes 18 which allow the solution to be separated to pass therethrough. Further, a wire netting 19 for collecting solid components is disposed over an inner peripheral surface of the basket 11. The screw 12 has such a contour approximately conformed to an inner peripheral surface of the basket 11, and is provided therein with a slurry-receiving space defined by a tapered inner wall surface thereof widened in diameter toward a hub portion (base) thereof. On a hub-side wall of the screw 12, there are provided a plurality of openings 20 through which the slurry is dispersed. The screw 12 is also provided on an outer peripheral surface thereof with helical blades. The basket 11 and the wire netting 19 constitute a filter member of the centrifugal separator.

The slurry received in a reservoir 21 shown in FIG. 4 is fed through the slurry feed pipe 14 toward a tip end 10a of the drive shaft 10, and introduced into an inner space (i.e., the slurry-receiving space) of the screw 12. At this time, the slurry is dispersed along the tapered inner peripheral surface of the screw 12 by the rotation of the screw 12, as shown in FIG. 5. As a result, the slurry is allowed to pass through the respective openings 20, dispersed in the circumferential direction of the wire netting 19 rotated at a high speed together with the basket 11, and impinged against the wire netting 19. The dispersion of the slurry in the circumferential direction of the wire netting 19 is also accelerated by the impingement of the slurry against the tip end 10*a* of the drive shaft 10. More specifically, the slurry is dispersed in the circumferential direction of the wire netting 19 by the impingement against the tip end 10*a*, and allowed to pass through the openings 20 and impinge against the wire netting 19 by the action of centrifugal force. Further, the slurry supplied over the wire netting 19 is caused to flow toward the tip end of the wire netting 19 by the action of both the tapered shape thereof, i.e., such a shape widened in diameter toward the tip end, and a rotating force thereof. The flowing movement of the slurry toward the tip end of the wire netting 19, is also accelerated by the scraping action of the helical blades which action is caused by the difference between rotating speeds of the helical blades.

The thus separated erythritol crystal is sprayed and washed with water fed through a wash water feed pipe 22 and then through the small holes 24 formed through the peripheral wall of the screw 12. Thereafter, the erythritol crystal is discharged by the screw 12 from the larger diameter end of the basket 11 to the outside of the system. On the other hand, a filtrate separated from the erythritol crystal and the waste wash water are flowed through the holes 18 into the casing 13, and then discharged through a drain pipe 23 to outside of the system.

By using the centrifugal separator having the above-mentioned structure, it becomes possible to filter the slurry while dispersing the slurry in the circumferential direction of the filtering surface. Accordingly, the erythritol crystal-containing slurry can be prevented from being divided into solid and liquid phases before the slurry is distributed over the whole filtering surface, so that it is possible to smoothly conduct the centrifugal separation of the slurry without uneven distribution of erythritol crystal.

In the centrifugal separator shown in FIGS. 4 and 5, the dispersion of the slurry in the circumferential direction of the filtering surface and the impingement of the slurry against the filtering surface, can be accomplished by using both (a) the effect of the tapered inner wall surface of the screw 12 and (b) the effect of the impingement of the slurry against the tip end 10*a* of the drive shaft 10, in combination with the action of centrifugal force. However, the similar condition can be accomplished by using either (a) or (b). Alternatively, there may also be adopted such a means that a ring-shaped member having a large number of openings or a rotating nozzle is fit to the tip end of the slurry feed pipe inserted into the smaller diameter side of the filter member, and the slurry is dispersed through the openings of the ring-shaped member or through the rotating nozzle in the circumferential direction of the filtering surface, and impinged against the filtering surface.

The centrifugal separators having such a structure that the slurry is dispersed in the circumferential direction of the filtering surface and then impinged against the filtering surface, are readily commercially available, for example, "CONTAVEX" or "PUSHER" (trade name, manufactured by SUMITOMO HEAVY MACHINERY INDUSTRY CO., LTD.).

Meanwhile, the crystal separation step may be usually conducted at as high a centrifugal force as possible in order to reduce a water content of the obtained crystal. However, according to the finding of the present inventors, since the erythritol crystal has a relatively large hardness, the operation at of excessive centrifugal force may result in fracture of the erythritol crystal due to the impingement against the inner wall surface of the centrifugal separator. For this reason, in accordance with the present invention, it is preferred that after the crystal separation step is conducted under a centrifugal force of usually 50 to 500 G, the obtained erythritol crystal is spray-washed with water which is used in an amount of 0.1 to 1 part by weight based on one part by weight of the erythritol crystal and maintained at a temperature of 5 to 20° C.

When the centrifugal force is less than 50 G, the water content of the obtained erythritol crystal may become too large, resulting in not only increased burden in the subsequent drying step, but also deterioration in quality of the obtained crystal product because of insufficient removal of the mother liquor therefrom. On the other hand, when the centrifugal force is more than 500 G, the erythritol crystal may be fractured upon the impingement against the inner wall surface of the centrifugal separator. Accordingly, the centrifugal force used in the crystal separation step is preferably 100 to 300 G.

The amount and temperature of the wash water used for the spray-washing may be determined such that a sufficient washing effect can be achieved without dissolving loss of the erythritol crystal even when the above-mentioned relatively small centrifugal force is used. Specifically, when the amount of the wash water used is less than 0.1 part by weight based on one part by weight of the erythritol crystal, the washing effect may be unsatisfactory, thereby failing to obtain a high-purity erythritol crystal. On the other hand, when the amount of the wash water used is more than 1 part by weight or when the temperature of the wash water is more than 20° C., the dissolving loss of erythritol crystal may become large, thereby rendering the process uneconomical. The amount of the wash water used is preferably 0.2 to 0.5 part by weight based on one part by weight of the erythritol crystal, and the temperature of the wash water is preferably 10 to 20° C.

The drying step of the process according to the present invention, is conducted in order to remove water from the erythritol crystal recovered from the preceding crystallization step. In the drying step, usually, there may be suitably used a fluidized bed-type dryer. Further, the sieving step is conducted in order to remove large size particles from the erythritol crystal. In the sieving step, there may be suitably used a vibrating screen device having a mesh size of usually 1,000 or 1,190 mm.

EXAMPLES

The present invention will now be described in more detail with reference to the following examples, but the present invention is not restricted to those examples and various modifications are possible within the scope of the invention.

Example 1

*Moniliella tomentosa var. pollinis* was added to a culture medium (culture solution) containing crystal glucose anhydride of 300 g/liter (calculated as glucose) and yeast extracts of 10 g/liter. The culture medium was subjected to shaking culture at 35° C. for 48 hours, thereby obtaining a seed culture medium (A). 1.2 liters of the obtained seed culture medium (A) was added to 600 liters of a culture medium containing crystal glucose anhydride of 300 g/liter (calculated as glucose) and corn-steep liquor of 37 g/liter. The cultivation was conducted at 35° C. and 1.0 kg/cm$^2$G for 48 hours while passing air therethrough at a feed rate of 300 liters/min and agitating at 300 rpm., thereby obtaining a seed culture medium (B). Next, 600 liters of the obtained seed culture medium (B) was added to 30 m$^3$ of a culture medium containing crystal glucose anhydride of 400 g/liter (calculated as glucose) and corn-steep liquor of 15 g/liter. The cultivation was conducted at 35° C. and 1.0 kg/cm$^2$G for 90 hours while passing air therethrough at a feed rate of 15 m$^3$/min and agitating at 100 rpm., and the cultivation was stopped when it was determined that glucose was completely consumed. Immediately after subjecting to heat-sterilization, the culture medium was treated by a cross-flow filtration method using a ceramic membrane, thereby separating microbe therefrom under the following conditions.

That is, first, as a microbe-concentration and separation procedure, an erythritol-containing culture solution heated to about 70° C. was fed to the circulation tank 1 used in the microbe-separating step (i.e., in the cross-flow filtration apparatus as shown in FIG. 1), and thereafter the pump 2 was operated to initiate circulation of the culture solution in which the solution was passed through the filter membrane 3 and the heat exchanger 6 and returned to the circulation tank 1. The purified solution (filtrate) passed through the filter membrane 3 was received in a filtrate reservoir 5. In the above procedure, the temperature and flow rate of the culture solution circulated was adjusted to about 70° C. and 5 m/s, respectively, and the pressure difference through membrane was adjusted to 1 Kg/cm$^2$. As a result, the average penetrating flow rate was 130 liters/m$^2$·hour.

Next, as a water-added filtration procedure, when the amount of the purified solution in the filtrate reservoir 5 reached 24 m$^3$, water was continuously fed into 6 m$^3$ of the concentrated solution in the circulation tank 1 while maintaining a constant level of the concentrated solution. While continuously feeding water to the circulation tank 1, the circulation of the culture solution was conducted in the same manner as described above, and the purified solution (filtrate) was received in the filtrate reservoir 5. Incidentally, water to be fed was preheated to about 70° C. before feeding to the circulation tank 1, if necessary. The total amount of water fed was 18 m$^3$, and the total amount of the purified solution (filtrate) received in the filtrate reservoir 5 was 18 m$^3$.

Next, as an additional concentration and filtration procedure, the circulation of the culture solution was continued in the same manner as described above even after stopping the feed of water, thereby receiving the purified solution (filtrate) in the filtrate reservoir 5. When the penetrating flow rate was reduced to about 50 liters/m$^2$·hour, the additional concentration and filtration procedure was stopped, and the cross-flow filtration apparatus was washed with water and regenerated for the succeeding microbe-separating step. The total amount of the purified solution (filtrate) received in the filtrate reservoir 5 in the above additional concentration and filtration procedure was 2 m$^3$.

The total amount of the purified solutions (filtrates) obtained in the above-mentioned respective procedures was 44 m$^3$, and the purified solution contained erythritol of 121 g/liter and glycerol of 0.3 g/liter.

Next, 44 m$^3$ of the obtained purified solution was passed through a tower filled with Na type of carboxylic acid-type weakly acidic cation exchange resins (trade name: DIAION WK-20produced by MITSUBISHI CHEMICAL CORP.) to replace hard components such as Ca and Mg with Na ions. At that time, the temperature of the purified solution was maintained at 70° C.

Next, the purified solution was concentrated until the solid content dissolved therein reached 40% by weight (primary concentration). As the evaporator, there was used a quadruple-effect evaporator equipped with shell and tube in a falling film-forming section thereof. The operation pressure was adjusted to 74 to 220 torr, and the fluid temperature was adjusted to 46 to 70° C. At that time, no foaming phenomenon was observed when the solution was concentrated under reduced pressure, and the concentration was able to be stably conducted.

Next, 1.44 m$^3$ of the obtained concentrated solution maintained at 70° C., was fed to a top of a separation tower having a size of 2,000 mm (diameter)×7,000 mm (height) and filled with Na type resins of divinyl benzene-crosslinked polystyrene sulfonic acid-type strongly acidic cation exchange resins (trade name: DIAION UBK-550, produced by MITSUBISHI CHEMICAL CORP.). The temperature of the separation tower was maintained at 70° C., and the concentrated solution was fed at a feed rate of 11.6 m$^3$/hour.

Successively, water was fed to the top of the separation tower at the same feed rate as that of the concentrated solution, and an effluent from the separation tower was divided into two fractions, front- and rear- fractions, by setting a boundary therebetween at a position where an effluent bed volume is 0.54. The amounts of the front- and rear-fractions were 4.8 m$^3$ and 3.4 m$^3$, respectively. Erythritol and glycerol were recovered as the rear-fraction. The above operation was repeated 10 times, thereby obtaining 34 m$^3$ of the rear-fraction in total. The obtained rear-fraction had such a composition that the erythritol concentration was 96.5 g/liter, the glycerol concentration was 0.2 g/liter and the concentration of the other substances was 2.0 g/liter.

Next, the rear-fraction was treated by successively passing through a tower filled with H type of strongly acidic cation exchange resins (trade name: DIAION SK1B, produced by MITSUBISHI CHEMICAL CORP.), a tower filled with OH type of weakly basic anion exchange resins (trade name: DIAION WA30, produced by MITSUBISHI CHEMICAL CORP.) and a mixed bed tower filled with both the above-mentioned H type of strongly acidic cation exchange resins and an OH type of weakly basic anion exchange resins (trade name: DIAION PA408, produced by MITSUBISHI CHEMICAL CORP.). Incidentally, the rear-fraction was preliminarily mixed with 8 m$^3$ of the wash water-containing crystallization mother liquor discharged from the crystal separation step (centrifugal separator) as described in detail hereinafter, before feeding to the tower filled with the H type of strongly acidic cation exchange resins. By recycling the crystallization mother liquor preliminarily mixed with the fraction, it is possible to recover erythritol contained therein. The thus treated solution was then mixed with 3.4 kg of activated carbon powder, and the mixture was stirred for 30 minutes and filtered to remove the activated carbon therefrom, thereby obtaining a filtrate.

The thus obtained filtrate was concentrated at 70° C. under reduced pressure until the solid content dissolved therein reached 53% by weight (erythritol concentration: 48.0% by weight) (secondary concentration). As the evaporator, there was used a quadruple-effect evaporator equipped with shell and tube at a falling film-forming section. The operation pressure was 74 to 220 torr, and the fluid temperature was 46 to 70° C. In the concentration step, no foaming phenomenon was observed when the solution was concentrated under reduced pressure, and the concentration was able to be stably conducted.

Next, the concentrated solution having a temperature of 70° C. was gradually cooled to 15° C. at a cooling rate of 7.5° C./hour. When the temperature of the concentrated solution reached 42° C. (difference from the saturation temperature (45° C.): −3° C.) in the course of the cooling, 380 g of a seed crystal of erythritol (weight percentage based on obtained erythritol crystal: 0.01% by weight) was added to the concentrated solution to grow an erythritol crystal, thereby obtaining an erythritol crystal-containing slurry.

Using a centrifugal separator (trade name "CONTAVEX", manufactured by SUMITOMO HEAVY MACHINERY INDUSTRY, CO., LTD.), the obtained erythritol crystal-containing slurry was centrifuged while applying a centrifugal force of 167 G thereto and while washing with water maintained at 15° C. in an amount of 0.2 part by weight based on one part by weight of a wet erythritol crystal, thereby separating the erythritol crystal from the slurry. More specifically, the erythritol crystal-containing slurry was dispersed in the circumferential direction of the filtering surface and then impinged against the filtering surface, thereby filtering out the erythritol crystal while spray-washing with water. As a result, 3.5 tons of erythritol crystal was obtained. The obtained erythritol crystal had a purity of 99.9% and a water content of 2.47% by weight. The crystallization mother liquor containing the wash water was circulated to a tank and temporarily stored therein to subsequently recover erythritol therefrom. Thereafter, the obtained erythritol crystal was dried.

The average particle size of the obtained erythritol crystal was measured and determined to be 750 μm. As a result of comparing the measured average particle size with that before subjecting to the centrifugal separation (750 μm), it was confirmed that no fracture of crystal was generated. The obtained erythritol crystal had mainly a single-crystal structure.

The respective purified solutions recovered from the microbe-separating step, the softening step, the concentration step before chromatographic separation (primary concentration) and the concentration step immediately before crystallization step (secondary concentration), were measured to determine absorbances thereof. The results are shown in Table 1. Incidentally, the measurement of absorbances was conducted by a spectrophotometer "UVIDEC-340" (manufactured by NIHON BUNKO CO., LTD.) using 1 cm quart cell and a wavelength of 720 nm or 420 nm.

The purified solutions recovered from the microbe-separating step and the softening step were subjected to a culture test. The results are shown in Table 1. Incidentally, in the culture test, a test solution sampled under sterilized conditions was placed in n incubator maintained at 25° C., and allowed to stand for one day and night. The test solution was visually observed to determine the growth of various germs in the test solution.

Further, the water content of the erythritol crystal and washing efficiency were also measured. The results are shown in Table 2. Incidentally, in Table 2, the contents of sugars and sugar alcohols were measured by a high-performance liquid chromatography, and part by weight in amount of wash water means part by weight based on one part by weight of wet erythritol crystal.

Reference Example 1

The same procedure as defined in Example 1 was conducted except that a centrifugal separator was used instead of the cross-flow filtration apparatus and the microbe separation was conducted while applying a centrifugal force of 8,000 G to the culture solution, thereby obtaining an erythritol crystal. A supernatant recovered from the microbe-separating step (centrifugal separator) was subjected to an absorbance measurement and a culture test in the same manner as in Example 1. The results are shown in Table 1.

Reference Example 2

The same procedure as defined in Example 1 was conducted except that the temperature of the microbe-separating step was changed from 70° C. to 25° C., thereby obtaining an erythritol crystal. A supernatant recovered from the microbe-separating step (centrifugal separator) was subjected to an absorbance measurement and a culture test in the same manner as in Example 1. The results are shown in Table 1.

Reference Example 3

The same procedure as defined in Example 1 was conducted except that the temperature of the softening step was changed from 70° C. to 25° C., thereby obtaining an erythritol crystal. In this case, the pressure loss of the feed pump for feeding the culture solution to be treated, to a resin-filled tower used in the softening step, was gradually increased. It was confirmed that the increase in pressure loss of the pump was caused by bacterial contamination of the culture solution. A purified solution recovered from the softening step was subjected to an absorbance measurement and a culture test in the same manner as in Example 1. The results are shown in Table 1.

Reference Example 4

The same procedure as defined in Example 1 was conducted except that the temperature of the softening step was changed from 70° C. to 45° C., thereby obtaining an erythritol crystal. A purified solution recovered from the softening step was subjected to an absorbance measurement and a culture test in the same manner as in Example 1. The results are shown in Table 1.

Reference Example 5

The same procedure as defined in Example 1 was conducted except that the temperature of the softening step was changed from 70° C. to 95° C., thereby obtaining an erythritol crystal. A purified solution recovered from the softening step was subjected to an absorbance measurement and a culture test in the same manner as in Example 1. The results are shown in Table 1.

Reference Example 6

The same procedure as defined in Example 1 was conducted except that the concentration step before chromatographic separation (primary concentration) and the concentration step immediately before crystallization step (secondary concentration) were conducted at an operation pressure of 30 torr and a fluid temperature of 30° C., thereby obtaining an erythritol crystal. In both of these concentration steps, violent foaming phenomenon was observed. A purified solution recovered from each concentration step was subjected to an absorbance measurement in the same manner as in Example 1. The results are shown in Table 1.

Reference Example 7

The same procedure as defined in Example 1 was conducted except that the concentration step before chromatographic separation (primary concentration) and the concentration step immediately before crystallization step (secondary concentration) were conducted at an operation pressure of 600 torr and a fluid temperature of 93° C., thereby obtaining an erythritol crystal. Although no foaming phenomenon was observed in any of these concentration steps, the solution after each concentration step was more remarkably colored as compared to that of Example 1. A purified solution recovered from each concentration step was subjected to an absorbance measurement in the same manner as in Example 1. The results are shown in Table 1.

Examples 2 to 3 and Reference Examples 8 to 11

The same procedure as defined in Example 1 was conducted except that the conditions used in the crystal separation step were changed to those shown in Table 2, thereby obtaining an erythritol crystal. The results of measurements of water content and washing efficiency of the obtained crystal, etc., are shown in Table 2.

TABLE 1

| Examples and Reference Examples | Microbe-separating step | | Softening step | |
|---|---|---|---|---|
| | A720 | Condition of germ growth | A420 | Condition of germ growth |
| Example 1 | 0.000 | – | 0.83 | – |
| Reference Example 1 | 0.327 | – | unmeasured | unmeasured |
| Reference Example 2 | 0.000 | + | unmeasured | unmeasured |
| Reference Example 3 | unmeasured | unmeasured | 0.69 | + |
| Reference Example 4 | unmeasured | unmeasured | 0.80 | + |
| Reference Example 5 | unmeasured | unmeasured | 0.94 | – |
| Reference Example 6 | unmeasured | unmeasured | unmeasured | unmeasured |
| Reference Example 7 | unmeasured | unmeasured | unmeasured | unmeasured |

| Examples and Reference Examples | After primary concentration A420 | After secondary concentration A420 |
|---|---|---|
| Example 1 | 13.9 | 0.030 |
| Reference Example 1 | unmeasured | unmeasured |
| Reference Example 2 | unmeasured | unmeasured |
| Reference Example 3 | unmeasured | unmeasured |
| Reference Example 4 | unmeasured | unmeasured |
| Reference Example 5 | unmeasured | unmeasured |
| Reference Example 6 | 12.9 | 0.027 |
| Reference Example 7 | 16.0 | 0.048 |

TABLE 2

| Examples and Reference Examples | Centrifugal force used (G) | Amount of wash water (part by weight) | Average particle size (μm) | |
|---|---|---|---|---|
| | | | Inside basket | After discharge |
| Example 1 | 167 | 0.2 | 750 | 750 |
| Example 2 | 296 | 0.2 | 760 | 740 |
| Example 3 | 167 | 0.3 | 750 | 745 |
| Reference Example 8 | 828 | 0.2 | 760 | 660 |
| Reference Example 9 | 527 | 0.2 | 760 | 700 |
| Reference Example 10 | 13 | 0.2 | 760 | 760 |
| Reference Example 11 | 167 | 0.05 | 750 | 750 |

| Examples and Reference Examples | Water content (wt. %) | Contents of sugar and sugar alcohol (wt. %) | | Washing efficiency |
|---|---|---|---|---|
| | | Before washing | After washing | |
| Example 1 | 2.47 | 0.70 | 0.07 | 90 |
| Example 2 | 2.15 | 0.77 | 0.09 | 88 |
| Example 3 | 2.35 | 0.93 | 0.13 | 86 |
| Reference Example 8 | 2.75 | 0.81 | 0.10 | 88 |
| Reference Example 9 | 2.32 | 0.75 | 0.08 | 89 |
| Reference Example 10 | 7.10 | 3.10 | 1.25 | 60 |
| Reference Example 11 | 2.24 | 0.75 | 0.37 | 49 |

Example 4

The same procedure as defined in Example 1 was conducted except that the procedure of the chromatographic separation step was changed as follows, thereby obtaining an erythritol crystal.

That is, the culturing step, the microbe-separating step, the softening step and the concentration step (primary concentration) were conducted in the same manner as in Example 1. Thereafter, the chromatographic separation step as shown in FIG. 3, i.e., the step using the separation tower comprising four series-connected towers each having a size of 2,000 mm (diameter)×1,750 mm (height) which was filled with 22 m³ of an Na type of divinyl benzene-crosslinked polystyrene sulfonic acid-type strongly acidic cation exchange resins (trade name: DIAION UBK-550, produced by MITSUBISHI CHEMICAL CORP.), was conducted in the following manner.

First, the above-mentioned concentrated solution maintained at 70° C. was fed to a top of the separation tower. The temperature of the separation tower was maintained at 70° C., and the feed rate of the concentration solution was adjusted to 11.9 m³/hour. The concentrated solution was divided into five fractions, and successively passed through the separation tower at the following five stages to recycle the overlapped fraction composed of an impurity fraction and an erythritol fraction.

<First Operation>

Valves 81 and 84 were opened, and 1.5 m³ of the concentrated solution stored in a tank 75 was fed to a top of the first tower 71 by operating a pump 91, thereby recovering 1.5 m³ of a product fraction (1) composed mainly of erythritol from the bottom of the fourth tower 74. Incidentally, the thus obtained product fraction was such a fraction-containing components eluted from the resin by moving the residual solution in the tower toward the bottom side thereof when the first operation was conducted following the fifth operation of the preceding cycle. After completion of the first operation, the valves 81 and 84 were closed (the valve closing operation was similarly performed after completion of each of subsequent operations).

<Second Operation>

Valves 87 and 82 were opened, and a pump 92 was operated to remove 6.4 m$^3$ of water from the bottom of the fourth tower 74 and circulate the removed water to the top of the first tower 71.

<Third Operation>

Valves 82 and 86 were opened, and the pump 92 was operated to feed 5.0 m$^3$ of water in a tank 76 to the top of the first tower 71 and remove 5.0 m$^3$ of a waste fraction from the bottom of the fourth tower 74. The waste fraction contained various salts, colored components and impurities.

<Fourth Operation>

1.0 m$^3$ of the overlapped fraction containing the erythritol fraction and the impurity fraction was removed from the bottom of the fourth tower 74 and circulated to the top of the first tower 71.

<Fifth Operation>

Valves 83 and 85 were opened, and the pump 92 was operated to feed 3.5 m$^3$ of water in the tank 76 to a top of the second tower 72 and recover 3.5 m$^3$ of a product fraction (2) composed mainly of erythritol from the bottom of the fourth tower 74. The total amount of the product fractions (1) and (2) was 5.0 m$^3$.

A series of the above-mentioned first to fifth operations as one cycle were repeated 7 times in which the fifth operation of the preceding cycle is followed by the first operation of the succeeding cycle, thereby obtaining 35.0 m$^3$ of the fraction composed mainly of erythritol. The obtained erythritol fraction had such a composition that the erythritol concentration was 97.2 g/liter, the glycerol concentration was 0.2 g/liter and the concentration of the other substances was 1.1 g/liter.

Next, the effluent recovered from the above chromatographic separation step was treated by successively passing through the tower filled with H type of strongly acidic cation exchange resins, the tower filled with OH type of weakly basic anion exchange resins and the mixed bed tower filled with both the above-mentioned H type of strongly acidic cation exchange resins and OH type of strongly basic anion exchange resins, in the same manner as in Example 1.

Further, the effluent was successively subjected to the concentration step (secondary concentration), the crystallization step and the crystal separation step, in the same manner as in Example 1, thereby obtaining 3.5 tons of erythritol crystal. The obtained erythritol crystal had a purity of 99.9% and a water content of 2.47% by weight. The crystallization mother liquor containing the wash water was recovered and temporarily stored in the tank to recover erythritol therefrom.

Thereafter, the obtained erythritol crystal was dried and measured to determine an average particle size thereof. As a result of the measurement, the average particle size was 750 μm. By comparing the average particle size with that before the centrifugal separation, it was confirmed that no fracture of the erythritol crystal was generated. The erythritol crystal had mainly a single-crystal structure.

In the above-mentioned operations, the erythritol fraction recovered from the chromatographic separation step was measured with respect to recovery percentage, impurity-removing percentage, decoloring percentage and desalting percentage of erythritol. The results are shown in Table 3. Incidentally, the recovery percentage and impurity-removing percentage of erythritol were calculated from values measured by a high-performance liquid chromatography. Also, the decoloring percentage and desalting percentage of erythritol were calculated from values obtained by measurements of absorbance (A420) and electric conductivity thereof.

Example 5

The same procedure as defined in Example 4 was conducted except that the cultivation was conducted in the following manner, thereby obtaining an high-purity erythritol crystal. That is, by using *Trichosporonoides megachiliensis* SN-G42 strain as erythritol-producing microorganisms, the seed culture medium (B) was obtained in the same manner as in Example 4. Thereafter, 600 liters of the obtained seed culture medium (B) was added to a culture solution containing purified glucose of 400 g/liter (calculated as glucose) and corn-steep liquor of 8 g/liter, and the cultivation was conducted at 35° C. and 1.0 kg/cm$^2$G for 90 hours while passing air therethrough at a feed rate of 15 m$^3$/min and stirring at 120 rpm. The amount of an effluent recovered from the chromatographic separation step (fraction composed mainly of erythritol) was 35.0 m$^3$. The effluent had such a composition that the erythritol concentration was 97.2 g/liter, the glycerol concentration was 0.2 g/liter and the concentration of unknown substances was 1.1 g/liter.

The effluent was subjected to the respective steps in the same manner as in Example 4, thereby obtaining 3.5 tons of erythritol crystal having a purity of 99.9%. The erythritol fraction recovered from the chromatographic separation step was measured with respect to recovery percentage, impurity-removing percentage, decoloring percentage and desalting percentage of erythritol in the same manner as in Example 4. The results are shown in Table 3.

Reference Example 12

The same procedure as defined in Example 4 was conducted except that the operations of the chromatographic separation step of Example 4 were changed as follows, thereby obtaining an erythritol crystal. That is, the overlapped fraction containing both erythritol fraction and impurity fraction was not circulated to the top of the first tower, but discharged together with the waste fraction by conducting the following chromatographic separation including a series of the first to fourth operations as one cycle. The results are shown in Table 3.

<First Operation: Same as the First Operation of Example 4>

Valves 81 and 84 were opened, and 1.5 m$^3$ of the concentrated solution stored in the tank 75 was fed to the top of the first tower 71 by operating the pump 91, thereby recovering 1.5 m$^3$ of the product fraction (1) composed mainly of erythritol from the bottom of the fourth tower 74. Incidentally, the thus obtained product fraction was such a fraction containing components eluted from the resin by moving the residual solution in the tower toward the bottom side thereof when the first operation was conducted following the fourth operation of the preceding cycle.

<Second Operation: Same as the Second Operation of Example 4>

Valves 82 and 87 were opened, and the pump 92 was operated to remove 6.4 m$^3$ of water from the bottom of the fourth tower 74 and circulate the removed water to the top of the first tower 71.

<Third Operation: Same as the Third Operation of Example 4 Except that the Amount of Water Fed was Changed>

Valves 82 and 86 were opened, and the pump 92 was operated to feed 6.0 m$^3$ of water in the tank 76 to the top of the first tower 71 and remove 6.0 m$^3$ of a waste fraction from the bottom of the fourth tower 74. The waste fraction contained various salts, colored components and impurities.

<Fourth Operation: Corresoonding to the Fifth Operation of Example 4>

Valves 83 and 85 were opened, and the pump 92 was operated to feed 3.5 m³ of water to the top of the second tower 72 and recover 3.5 m³ of the product fraction (2) composed mainly of erythritol from the bottom of the fourth tower 74. The total amount of the product fractions (1) and (2) recovered was 5.0 m³.

Reference Example 13

The same procedure as defined in Example 4 was conducted except that the operations of the chromatographic separation step of Example 4 were changed as follows, thereby obtaining an erythritol crystal. That is, the overlapped fraction containing both erythritol fraction and impurity fraction was not circulated to the top of the first tower, but recovered together with the product fraction by conducting the following chromatographic separation including a series of first through fourth operations as one cycle. The results are shown in Table 3.

<First Operation: Same as the First Operation of Example 4>

Valves 84 and 82 were opened, and 1.5 m³ of the concentrated solution stored in the tank 75 was fed to the top of the first tower 71 by operating the pump 91, thereby recovering 1.5 m³ of the product fraction (1) composed mainly of erythritol from the bottom of the fourth tower 74. Incidentally, the thus obtained product fraction was such a fraction containing components eluted from the resin by moving a residual solution in the tower toward the bottom side thereof when the first operation was conducted following the fourth operation of the preceding cycle.

<Second Operation: Same as the Second Operation of Example 4>

Valves 82 and 87 were opened, and the pump 92 was operated to remove 6.4 m³ of water from the bottom of the fourth tower 74 and circulate the removed water to the top of the first tower 71.

<Third Operation: Same as the Third Operation of Example 4>

Valves 82 and 86 were opened, and the pump 92 was operated to feed 5.0 m³ of water in the tank 76 to the top of the first tower 71 and remove 5.0 m³ of a waste fraction from the bottom of the fourth tower 74. The waste fraction contained various salts, colored components and impurities.

<Fourth Operation: Almost Same as the Fifth Operation of Example 4 Except that the Amount of Water Fed was Changed>

Valves 83 and 85 were opened, and the pump 92 was operated to feed 4.5 m³ of water in the tank 76 to the top of the second tower 72 and recover 4.5 m³ of the product fraction (2) composed mainly of erythritol from the bottom of the fourth tower 74. The total amount of the product fractions (1) and (2) recovered was 6.0 m³.

Reference Example 14

The same procedure as defined in Example 4 was conducted except that the operations of the chromatographic separation step of Example 4 were changed as follows, thereby obtaining an erythritol crystal. That is, the overlapped fraction containing both erythritol fraction and impurity fraction was not circulated to the top of the first tower, but a part of the overlapped fraction was recovered together with the product fraction and the remaining part thereof was discharged together with the waste fraction by conducting the following chromatographic separation including a series of first to fourth operations as one cycle. The results are shown in Table 3.

<First Operation: Same as the First Operation of Example 4>

Valves 84 and 82 were opened, and 1.5 m³ of the concentrated solution stored in the tank 75 was fed to the top of the first tower 71 by operating the pump 91, thereby recovering 1.5 m³ of the product fraction (1) composed mainly of erythritol from the bottom of the fourth tower 74. Incidentally, the thus obtained product fraction was such a fraction containing components eluted from the resin by moving a residual solution in the tower toward the bottom side thereof when the first operation was conducted following the fourth operation of the preceding cycle.

<Second Operation: Same as the Second Operation of Example 4>

Valves 82 and 87 were opened, and the pump 92 was operated to remove 6.4 m³ of water from the bottom of the fourth tower 74 and circulate the removed water to the top of the first tower 71.

<Third Operation: Same as the Third Operation of Example 4 Except that the Amount of Water Fed was Changed>

Valves 82 and 86 were opened, and the pump 92 was operated to feed 5.5 m³ of water in the tank 76 to the top of the first tower 71 and remove 5.5 m³ of a waste fraction from the bottom of the fourth tower 74. The waste fraction contained various salts, colored components and impurities.

<Fourth Operation: Almost Same as the Fifth Operation of Example 4 Except that the Amount of Water Fed was Changed>

Valves 83 and 85 were opened, and the pump 92 was operated to feed 4.0 m³ of water in the tank 76 to the top of the second tower 72 and recover 4.0 m³ of the product fraction (2) composed mainly of erythritol from the bottom of the fourth tower 74. The total amount of the product fractions (1) and (2) recovered was 5.5 m³.

TABLE 3

| Examples and Reference Examples | Method of treating overlapped fraction | Recovery percentage of erythritol (%) |
|---|---|---|
| Example 4 | Recycled | 99.9 |
| Example 5 | Recycled | 99.9 |
| Reference Example 12 | Mixed with waste fraction | 95 |
| Reference Example 13 | Mixed with product fraction | 99.9 |
| Reference Example 14 | Divided into a part mixed with product fraction and the remaining part mixed with waste fraction | 97 |

| Examples and Reference Examples | Impurity-removing percentage (%) | Decoloring percentage (%) | Desalting percentage (%) |
|---|---|---|---|
| Example 4 | 92 | 93 | 99 |
| Example 5 | 92 | 93 | 99 |
| Reference Example 12 | 92 | 93 | 99 |
| Reference Example 13 | 82 | 89 | 97 |
| Reference Example 14 | 87 | 91 | 98 |

Example 6

The same procedure as defined in Example 1 was conducted except that when the temperature of the concentrated solution in the crystallization step reached 44° C. (difference from the saturation temperature (45° C.): −10° C.) in the course of the cooling, 640 g of a seed crystal of erythritol (weight percentage based on obtained crystal: 0.02% by weight) was added to the concentrated solution, thereby obtaining an erythritol crystal. It was confirmed that the average particle size and shape of the obtained erythritol crystal were the same as those of Example 1.

Reference Example 15

The same procedure as defined in Example 1 was conducted except that the cooling rate used for gradually cooling the concentration solution to 15° C., was changed to 25.0° C./hour, thereby obtaining an erythritol crystal. It was confirmed that the average particle size of the obtained erythritol crystal was the same as that of Example 1, but the erythritol crystal was mainly present in the form of coagulated crystals.

Reference Example 16

The same procedure as defined in Example 1 was conducted except that a vertical basket-type centrifugal separator was used and the erythritol crystal-containing slurry was fed through a single-pipe nozzle thereinto, thereby obtaining an erythritol crystal. The centrifugal force used was 167 G. In this Reference Example, the erythritol crystal-containing slurry fed through the single-pipe nozzle was divided into liquid and solid phases before being distributed over the whole filtering surface, resulting in uneven distribution of the slurry in the centrifugal separator and failed operation of the apparatus.

What is claimed is:

1. A process for producing a high-purity erythritol crystal, comprising steps of:
    a microbe-separating step of separating microbe from an erythritol-containing culture solution as a raw solution;
    a chromatographic separation step of subjecting a purified solution recovered from said microbe-separating step to chromatographic separation; and
    a crystallization step of subjecting an erythritol fraction recovered from said chromatographic separation step to crystallization, thereby obtaining an erythritol crystal,
    wherein said microbe-separating step is conducted by a cross-flow filtering method using a ceramic membrane or an organic membrane maintaining the temperature of said solution treated being maintained at 50 to 90° C.

2. A process for producing a high-purity erythritol crystal, comprising steps of:
    a crystallization step of subjecting an erythritol-containing aqueous solution to crystallization; and
    a crystal separation step of separating an erythritol crystal from an erythritol crystal-containing slurry recovered from said crystallization step,
    wherein said crystal separation step is conducted by a centrifugal separator of a type in which a slurry is dispersed in the circumferential direction of a filtering surface and impinged against the filtering surface.

3. A process according to claim 2, which further comprises a microbe-separating step of separating microbe from an erythritol-containing culture solution as a raw solution and a chromatographic separation step of subjecting a purified solution recovered from said microbe-separating step to chromatographic separation, followed by said crystallization step,
    said erythritol-containing aqueous solution to be treated in said crystallization step being an erythritol fraction recovered from said chromatographic separation step.

4. A process according to claim 3, wherein said erythritol-containing aqueous solution is a crystallization mother liquor recovered from said crystal separation step.

5. A process for producing a high-purity erythritol crystal, comprising steps of:
    a crystallization step of subjecting an erythritol-containing aqueous solution to crystallization; and
    a crystal separation step of separating an erythritol crystal from an erythritol crystal-containing slurry obtained in said crystallization step,
    wherein said crystal separation step is conducted by centrifugal separation using a centrifugal force of 50 to 500 torr; a wet erythritol crystal separated by said centrifugal separation is spray-washed with water at a temperature of not more than 20° C.; and the amount of water used for the spray-washing is 0.1 to 1 part by weight based on one part by weight of said wet erythritol crystal.

6. A process according to claim 5, which further comprises a microbe-separating step of separating microbe from an erythritol-containing culture solution as a raw solution and a chromatographic separation step of subjecting a purified solution recovered from said microbe-separating step to chromatographic separation, followed by said crystallization step,
    said erythritol-containing aqueous solution to be treated in said crystallization step being an erythritol fraction recovered from said chromatographic separation step.

7. A process according to claim 6, wherein said erythritol-containing aqueous solution is a crystallization mother liquor recovered from said crystallization step.

* * * * *